United States Patent
Lee et al.

(10) Patent No.: US 11,543,443 B2
(45) Date of Patent: Jan. 3, 2023

(54) IMPEDANCE MEASURING APPARATUS

(71) Applicants: SAMSUNG ELECTRONICS CO., LTD., Suwon-si (KR); Korea Advanced Institute of Science and Technology, Daejeon (KR)

(72) Inventors: Wonseok Lee, Suwon-si (KR); Ji-Hoon Suh, Daejeon (KR); Minkyu Je, Daejeon (KR); Sang Joon Kim, Hwaseong-si (KR)

(73) Assignees: Samsung Electronics Co., Ltd., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 42 days.

(21) Appl. No.: 17/355,375

(22) Filed: Jun. 23, 2021

(65) Prior Publication Data

US 2022/0120797 A1    Apr. 21, 2022

(30) Foreign Application Priority Data

Oct. 16, 2020    (KR) ........................ 10-2020-0134627

(51) Int. Cl.
*G01R 27/16*    (2006.01)
*G01N 27/02*    (2006.01)
(Continued)

(52) U.S. Cl.
CPC ........... *G01R 27/16* (2013.01); *G01N 27/028* (2013.01); *H03M 1/001* (2013.01); *A61B 5/053* (2013.01)

(58) Field of Classification Search
CPC ........ G01R 27/00; G01R 27/02; G01R 27/16; G01R 19/00; G01R 19/25; G01R 29/00;
(Continued)

(56) References Cited

U.S. PATENT DOCUMENTS 6,047,208 A  *  4/2000  Flower ............... A61N 1/30
                                                  604/20
7,896,807 B2     3/2011  Clancy et al.
(Continued)

FOREIGN PATENT DOCUMENTS

CN    203746014 U  *  7/2014  ............. G06F 3/044
KR    10-0708939 B1    4/2007
(Continued)

OTHER PUBLICATIONS

Hong, et al. "A 4.9 mΩ-Sensitivity Mobile Electrical Impedance Tomography IC for Early Breast-Cancer Detection System." *IEEE Journal of Solid-State Circuits* 50.1 (Jan. 1, 2015): 245-257. (13 pages in English).

(Continued)

*Primary Examiner* — Hoai-An D. Nguyen
(74) *Attorney, Agent, or Firm* — NSIP Law

(57) ABSTRACT

An impedance measuring apparatus is disclosed. The impedance measuring apparatus includes an input current generator configured to generate a sinusoidal input signal of a carrier frequency, a first electrode configured to apply the sinusoidal input signal to an object which has an impedance, a second electrode configured to receive an amplitude modulated signal from the object, a first amplifier configured to amplify the received amplitude modulated signal and output a first amplified signal, a baseline signal subtractor configured to subtract a baseline signal generated based on the first amplified signal from the amplitude modulated signal and output a subtraction modulated signal, an analog-to-digital converter (ADC) configured to convert the subtraction modulated signal to a digital modulated signal, and an impedance measurer configured to measure the impedance based on the digital modulated signal.

13 Claims, 6 Drawing Sheets

(51) Int. Cl.
  *H03M 1/00* (2006.01)
  *A61B 5/053* (2021.01)

(58) Field of Classification Search
  CPC ........ G01R 29/02; G01N 27/00; G01N 27/02;
    G01N 27/028; A61B 5/00; A61B 5/05;
    A61B 5/053; A61B 5/0531; A61B
    5/0536; A61B 5/0537; A61B 5/48; A61B
    5/4869; A61B 5/72; A61B 5/7225; H03M
    1/00; H03M 1/001
  See application file for complete search history.

(56) References Cited

U.S. PATENT DOCUMENTS

| | | | | |
|---|---|---|---|---|
| 7,940,038 B2* | 5/2011 | Da Silva | ............ | G01N 33/2823 |
| | | | | 324/715 |
| 9,060,700 B2* | 6/2015 | Cho | ................... | A61B 5/14532 |
| 10,120,005 B2* | 11/2018 | Cherkassky | ......... | A61B 5/7278 |
| 10,702,183 B2 | 7/2020 | Harrison | | |
| 2001/0030546 A1* | 10/2001 | Yamada | ............... | A61B 5/4869 |
| | | | | 324/691 |
| 2009/0102450 A1* | 4/2009 | Da Silva | ................ | G01N 27/07 |
| | | | | 324/72 |
| 2010/0308907 A1 | 12/2010 | Xiang et al. | | |
| 2018/0321302 A1* | 11/2018 | Qu | ..................... | G01R 31/2829 |
| 2019/0369726 A1 | 12/2019 | Kang et al. | | |

FOREIGN PATENT DOCUMENTS

| KR | 10-2018-0062975 A | 6/2018 |
|---|---|---|
| KR | 10-2077619 B1 | 2/2020 |

OTHER PUBLICATIONS

Aristovich, et al. "Imaging fast neural traffic at fascicular level with electrical impedance tomography: proof of principle in rat sciatic nerve." *Journal of neural engineering* 15.5 (2018): 056025. (13 pages in English).

Ha, et al. "A Bio-Impedance Readout IC With Digital-Assisted Baseline Cancellation for Two-Electrode Measurement." *IEEE Journal of Solid-State Circuits* 54.11 (Nov. 11, 2019): 2969-2979. (11 pages in English).

* cited by examiner

IMPEDANCE MEASURING APPARATUS

CROSS-REFERENCE TO RELATED APPLICATIONS

This application claims the benefit under 35 USC § 119(a) of Korean Patent Application No. 10-2020-0134627 filed on Oct. 16, 2020, in the Korean Intellectual Property Office, the entire disclosure of which is incorporated herein by reference for all purposes.

BACKGROUND

1. Field

The following description relates to impedance measurement, and more particularly, to an impedance measuring apparatus.

2. Description of Related Art

A bioelectrical impedance analysis (BIA) is a technology that measures human body water using an electrical method. When a weak alternating current (AC) signal is sent to a human body, a current may flow along highly conductive body water. An amount of the water may determine a width of a path through which electricity flows, which is represented as a measured value referred to as an impedance.

An amount of human body water may be obtained by calculating a bioelectrical impedance value, and an amount of protein and an amount of minerals may be obtained from the amount of human body water. An amount of body fat may then be obtained by subtracting the amount of protein and the amount of minerals from the amount of human body water. Thus, by measuring such a bioelectrical impedance, clinical information including, for example, human body fat, may be obtained.

The above information is presented as background information only to assist with an understanding of the present disclosure. No determination has been made, and no assertion is made, as to whether any of the above might be applicable as prior art with regard to the disclosure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, an impedance measuring apparatus includes an input current generator, configured to generate a sinusoidal input signal of a carrier frequency; a first electrode, configured to apply the sinusoidal input signal to an object which has an impedance; a second electrode, configured to receive an amplitude modulated signal from the object; a first amplifier, configured to amplify the received amplitude modulated signal and output a first amplified signal; a baseline signal subtractor, configured to subtract a baseline signal generated based on the first amplified signal from the amplitude modulated signal, and output a subtraction modulated signal; an analog-to-digital converter (ADC), configured to convert the subtraction modulated signal to a digital modulated signal; and an impedance measurer, configured to measure the impedance based on the digital modulated signal.

The baseline signal subtractor may include a baseline signal generator, configured to generate the baseline signal based on the first amplified signal; and a baseline subtraction circuit, configured to subtract the baseline signal from the amplitude modulated signal.

The baseline signal generator may include an amplitude estimation circuit, configured to estimate an amplitude of the baseline signal from the first amplified signal; and a phase extraction circuit, configured to extract a phase of the baseline signal from the first amplified signal.

The apparatus may further include a digital demodulator configured to convert the digital modulated signal to a digital demodulated signal of an impedance frequency by removing a component of the carrier frequency from the digital modulated signal, wherein the impedance measurer is configured to measure the impedance based on the digital demodulated signal.

The apparatus may further include a buffer, configured to receive the subtraction modulated signal, and output the received subtraction modulated signal.

The apparatus may further include a second amplifier, configured to amplify the subtraction modulated signal, and output a second amplified signal, wherein the ADC is configured to convert the second amplified signal to the digital modulated signal, and wherein a gain of the second amplifier is adjustable.

The apparatus may further include an analog demodulator, configured to convert the subtraction modulated signal to a first analog demodulated signal of an impedance frequency by removing a component of the carrier frequency from the subtraction modulated signal, wherein the ADC is configured to convert the first analog demodulated signal to the digital modulated signal.

The apparatus may further include a filter, configured to filter a high-frequency component that excludes the impedance frequency out of the first analog demodulated signal, and output a second analog demodulated signal, wherein the ADC is configured to convert the second analog demodulated signal to the digital modulated signal.

In a general aspect, an impedance measuring apparatus includes an input current generator, configured to generate a sinusoidal input signal of a carrier frequency; a plurality of electrode pairs configured to apply the sinusoidal input signal to an object which has an impedance, and receive an amplitude modulated signal from the object; and one or more signal processors corresponding to a channel corresponding to each of the electrode pairs, wherein each of the electrode pairs includes a first electrode, configured to apply the sinusoidal input signal to the object which has the impedance; and a second electrode, configured to receive the amplitude modulated signal from the object, and the signal processor includes a first amplifier, configured to amplify the amplitude modulated signal and output a first amplified signal; a baseline signal subtractor, configured to subtract a baseline signal generated based on the first amplified signal from the amplitude modulated signal, and output a subtraction modulated signal; an analog-to-digital converter (ADC), configured to convert the subtraction modulated signal to a digital modulated signal; and an impedance measurer, configured to measure the impedance based on the digital modulated signal.

The input current generator may include a digital-to-analog converter (DAC) configured to generate the sinusoidal input signal of the carrier frequency; and a memory configured to store an analog level of the sinusoidal input signal, wherein the baseline signal subtractor is configured to generate the baseline signal based on the first amplified signal and the analog level.

In a general aspect, an impedance measuring method of an impedance measuring apparatus includes generating, by an input current generator, a sinusoidal input signal of a carrier frequency; applying, by a first electrode, the sinusoidal input signal to an object; receiving, by a second electrode, an amplitude modulated signal from the object; amplifying, by an amplifier the received amplitude modulated signal to output a first amplified signal; subtracting, by a baseline signal subtractor, a baseline signal generated based on the first amplified signal from the amplitude modulated signal, and output a subtraction modulated signal; converting, by an analog-to-digital (ADC), the subtraction modulated signal to a digital modulated signal; and measuring, by an impedance measurer, the impedance based on the digital modulated signal.

The baseline signal may be generated based on the amplitude modulated signal from the object, and the baseline signal may be subtracted from the amplitude modulated signal to measure the impedance of the object.

The impedance of the object may be measured through a plurality of channels corresponding to a plurality of electrode pairs.

Other features and aspects will be apparent from the following detailed description, the drawings, and the claims.

BRIEF DESCRIPTION OF DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
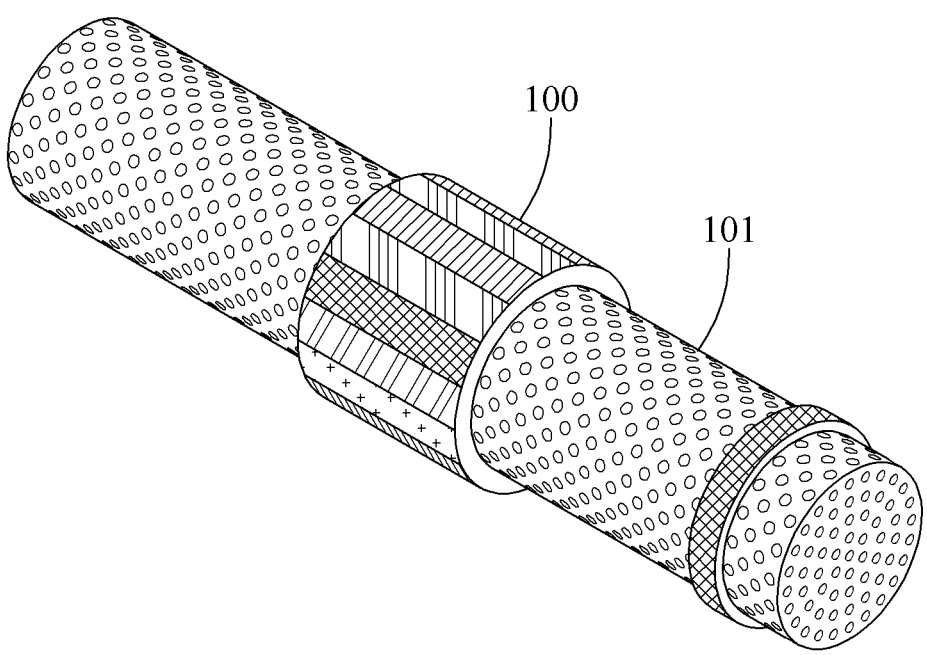
FIG. 1 is a diagram illustrating an example in which an impedance of an object is measured by an impedance measuring apparatus, in accordance with one or more embodiments.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness, noting that omissions of features and their descriptions are also not intended to be admissions of their general knowledge.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Throughout the specification, when an element, such as a layer, region, or substrate is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

The terminology used herein is for the purpose of describing particular examples only, and is not to be used to limit the disclosure. As used herein, the singular forms "a," "an," and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof.

In addition, terms such as first, second, A, B, (a), (b), and the like may be used herein to describe components. Each of these terminologies is not used to define an essence, order, or sequence of a corresponding component but used merely to distinguish the corresponding component from other component(s).

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

Unless otherwise defined, all terms, including technical and scientific terms, used herein have the same meaning as commonly understood by one of ordinary skill in the art to which this disclosure pertains and after an understanding of the disclosure of this application. Terms, such as those defined in commonly used dictionaries, are to be interpreted as having a meaning that is consistent with their meaning in the context of the relevant art and the disclosure of this application, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Hereinafter, examples will be described in detail with reference to the accompanying drawings, and like reference numerals in the drawings refer to like elements throughout.

FIG. 1 is a diagram illustrating an example in which an impedance of an object is measured by an impedance measuring apparatus, in accordance with one or more embodiments.

An impedance measuring apparatus 100 may measure an impedance of an object 101. The impedance measuring apparatus 100 may generate a baseline signal based on an amplitude modulated signal received from the object 101, and subtract the baseline signal from the amplitude modulated signal, thereby more accurately measuring the impedance of the object 101.

The impedance measuring apparatus 100 may be applied or implemented to measure a bioimpedance. In an example, the impedance measuring apparatus 100 may be implemented to measure an impedance of a nerve fascicle. The impedance measuring apparatus 100 may be implemented to perform electrical impedance tomography (EIT). The impedance measuring apparatus 100 may be applicable to all fields that need the measurement of a small change in an impedance, for example, and not limited to, a sensor for a robot, in addition to implementation in the medical field. The impedance measuring apparatus 100 may be embodied, as an example, in a form of a chip. Herein, it is noted that use of the term 'may' with respect to an example or embodiment, e.g., as to what an example or embodiment may include or implement, means that at least one example or embodiment exists where such a feature is included or implemented while all examples and embodiments are not limited thereto.

To measure an impedance, a current may be applied to a measurement target, and a voltage generated at both ends of the measurement target may then be measured. An output signal may include a baseline signal that occurs on an input signal of a carrier frequency, in addition to a target signal of a low frequency to which a characteristic of the measurement target is applied. When amplifying the output signal to detect the target signal, the baseline signal may also be amplified. In general, the baseline signal may have an amplitude greater than an amplitude of the target signal, and thus an amplified portion of the target signal may have a low resolution. In an example in which a nominal value of an impedance to be measured is great, an impedance value that changes finely or minimally may not be easy to measure, and thus a high-performance amplifier and analog-to-digital converter (ADC) may be implemented.

When applying a square-wave input signal to the measurement target to subtract the baseline signal, there may be a signal component by harmonic frequencies in addition to a frequency of the target signal which is the measurement target from which an impedance is to be measured. Thus, noise may be generated from a component of the harmonic frequencies due to the nonlinearity of an amplifier in an impedance measurement circuit, or due to a demodulator.

In an example, the impedance measuring apparatus 100 may generate a baseline signal based on an amplitude modulated signal, and subtract the baseline signal from the amplitude modulated signal. Thus, it is possible to use maximally an input range of an amplifier and enable high-resolution impedance measurement. Additionally, the impedance measuring apparatus 100 may generate a sinusoidal or pseudo-sinusoidal baseline signal and subtract the baseline signal from the amplitude modulated signal, and thus reduce noise occurring due to a harmonic frequency component.

Accordingly, the impedance measuring apparatus 100 may generate the baseline signal by estimating an amplitude and a phase of the amplitude modulated signal. The impedance measuring apparatus 100 may then detect the target signal to which a characteristic of the object 101 is applied by subtracting the baseline signal from the amplitude modulated signal. The impedance measuring apparatus 100 may amplify a signal obtained by subtracting the baseline signal, and measure an amount of a minute change (or a minute variation) in an impedance.

When using such a sinusoidal or pseudo-sinusoidal input signal, an amplitude and a phase of a baseline signal to be subtracted may need to be determined accurately to precisely subtract the baseline signal. The baseline signal may be accurately subtracted when a phase of the input signal and the phase of the baseline signal to be subtracted are matched to each other. The impedance measuring apparatus 100 may roughly verify the amplitude of the input signal through an amplitude estimation circuit and extract the phase of the baseline signal through a phase extraction circuit. The impedance measuring apparatus 100 may perform scaling on a sinusoidal amplitude generated from a digital-to-analog converter (DAC) based on the estimated amplitude and generate the baseline signal by synchronizing the sinusoidal signal with the estimated phase.

In another example, the impedance measuring apparatus 100 may measure an impedance of the object 101 through a plurality of channels corresponding to a plurality of electrode pairs 226, 228. The electrode pairs 226, 228 may be arranged along a longitudinal direction of the object 101, and, in an example, may be arranged to surround the object 101. Since the channels may be arranged in different portions of the object 101, the impedance measuring apparatus 100 may measure the impedance of the object 101 more accurately.

To measure an impedance through a plurality of channels as in tomography, a pseudo-sinusoidal input signal may be applied to each of the channels. In such an example, when using a high-resolution DAC to generate a high-quality baseline signal to be subtracted for each of the channels, a determined area may increase, which may be an adverse factor in measuring a bioimpedance.

The impedance measuring apparatus 100 may share a single high-resolution signal generator to generate a high-resolution baseline signal in the channels. The high-resolution signal generator may include a DAC. A memory may store an analog level of a high-resolution signal generated by the DAC, and continuously refresh or update it. Based on analog levels of high-resolution pseudo-sinusoidal signals stored in the memory, a baseline signal may be generated based on an amplitude and a phase to be suitable to an input signal in each of the channels.

As described above, the impedance measuring apparatus 100 may store pseudo-sinusoidal analog levels generated in the DAC to generate an input signal, instead of generating a baseline signal by arranging a high-resolution DAC for each channel. The impedance measuring apparatus 100 may generate a baseline signal of each channel by outputting the stored analog levels in sequential order based on time.

Although what has been described above pertains to measuring an impedance by applying a current and measuring a voltage, it is also possible to measure an impedance by applying a voltage and measuring a current.

Figure 2:
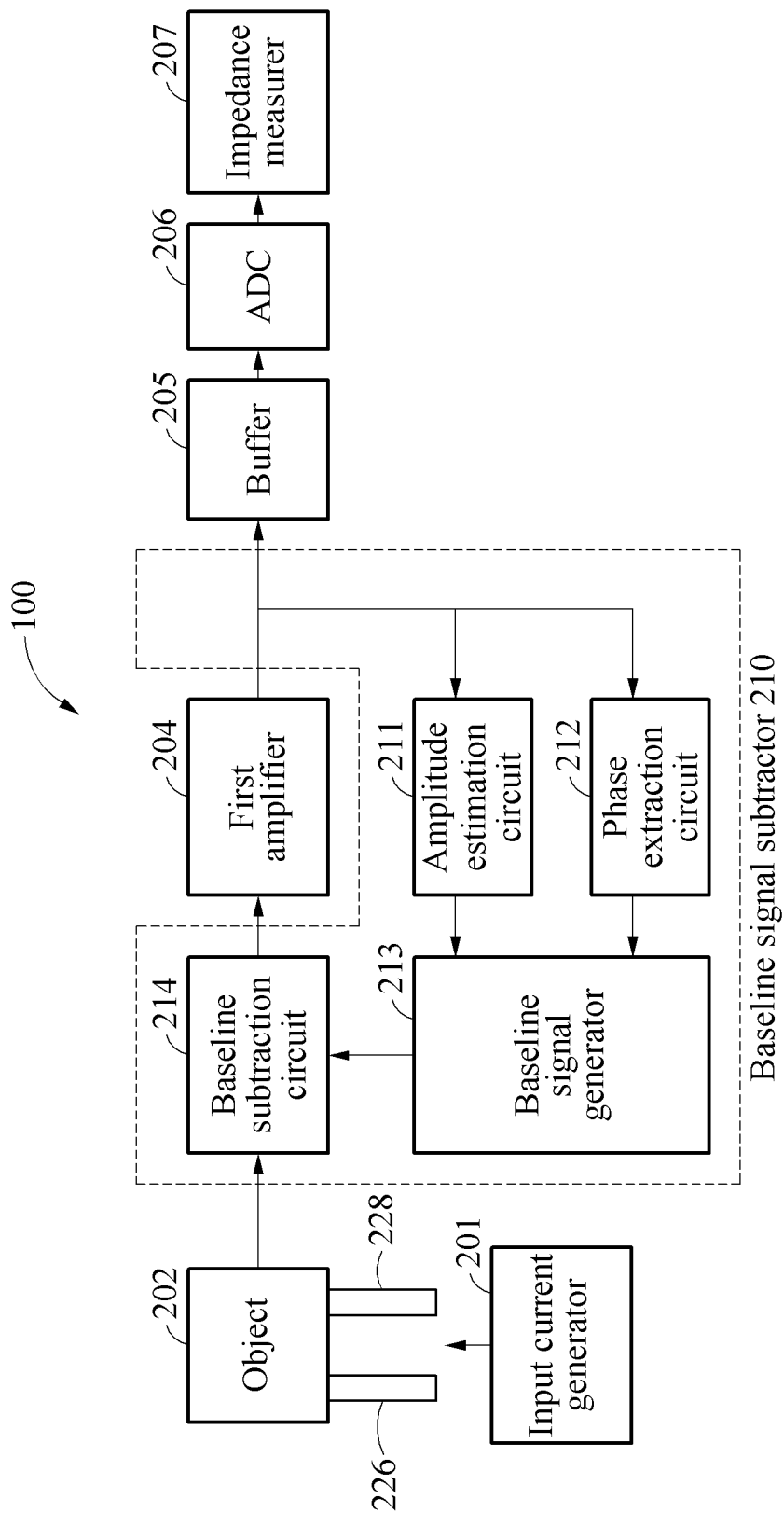
FIG. 2 is a diagram illustrating an example of a configuration of an impedance measuring apparatus, in accordance with one or more embodiments.

FIG. 2 is a diagram illustrating an example of a configuration of an impedance measuring apparatus, in accordance with one or more embodiments.

Referring to FIG. 2, the impedance measuring apparatus 100 includes an input current generator 201, a first electrode 226), a second electrode 228, a first amplifier 204, a baseline signal subtractor 210, an ADC 206, and an impedance measurer 207.

The input current generator 201 may generate a sinusoidal input signal of a carrier frequency. The first electrode 226 may apply the sinusoidal input signal to an object 202 having an impedance. The second electrode 228 may receive an amplitude modulated signal from the object 202. The impedance measuring apparatus 100 may apply a sinusoidal or pseudo-sinusoidal input signal to the object 202, thereby reducing noise occurring due to a harmonic frequency component.

The first amplifier 204 may amplify the amplitude modulated signal to output a first amplified signal. Rather than obtaining amplitude and phase information immediately from the amplitude modulated signal, the first amplifier 204 may amplify the amplitude modulated signal to implement amplitude estimation and phase extraction more accurately. Based on the first amplified signal that is obtained by being amplified to have a sufficient magnitude through the first amplifier 204, the amplitude estimation and the phase extraction may be performed more accurately.

The baseline signal subtractor 210 may subtract a baseline signal generated based on the first amplified signal from the amplitude modulated signal to output a subtraction modulated signal. The baseline signal subtractor 210 includes a baseline signal generator 213 and a baseline subtraction circuit 214. The baseline signal generator 213 may generate the baseline signal based on the first amplified signal. The baseline subtraction circuit 214 may subtract the baseline signal from the amplitude modulated signal. The baseline signal generator 213 includes an amplitude estimation circuit 211 and a phase extraction circuit 212. The amplitude estimation circuit 211 may estimate an amplitude of the baseline signal from the first amplified signal. The phase extraction circuit 212 may extract a phase of the baseline signal from the first amplified signal. As described above, by subtracting, from the amplitude modulated signal, the baseline signal which is a carrier frequency component of the input signal, the impedance measuring apparatus 100 may maximally use an input range of an amplifier and perform high-resolution impedance measurement.

The ADC 206 may convert the subtraction modulated signal to a digital modulated signal. The impedance measurer 207 may measure the impedance based on the digital modulated signal.

The impedance measuring apparatus 100 may further include a digital demodulator (not shown). The digital demodulator may convert the digital modulated signal to a digital demodulated signal of an impedance frequency by removing the carrier frequency component from the digital modulated signal. In such an example, the impedance measurer 207 may measure the impedance based on the digital demodulated signal.

The impedance measuring apparatus 100 may further include a buffer 205. The ADC 206 may receive the subtraction modulated signal from the buffer 205. Based on the implementation of the buffer 205, an input resistance of the ADC 206 may increase.

Figure 3:
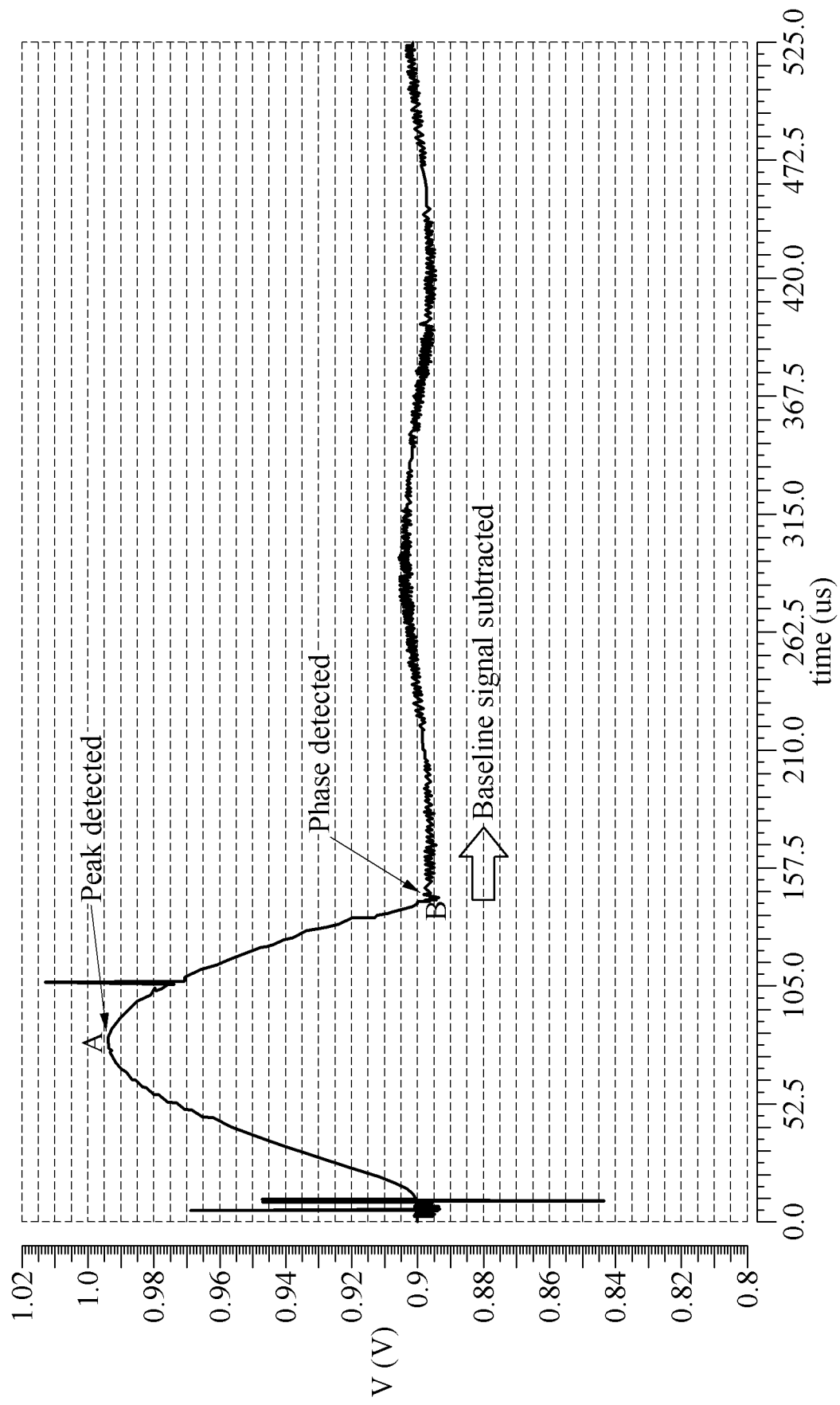
FIG. 3 is a graph illustrating an example of a voltage of a signal input to a first amplifier of an impedance measuring apparatus, in accordance with one or more embodiments.

FIG. 3 is a graph illustrating an example of a voltage of a signal input to a first amplifier of an impedance measuring apparatus, in accordance with one or more embodiments.

The impedance measuring apparatus 100 may measure a minute impedance variation of a target signal to which a characteristic of an object (e.g., the object 101 of FIG. 1) is applied by amplifying a signal from which a baseline signal is subtracted. Here, the minute impedance variation may refer to an amount of a minute change in an impedance. Referring to FIG. 3, an amplitude modulated signal from which a baseline signal is not yet subtracted may be received until a point B. Due to a component of the baseline signal, a component of a target signal included in the amplitude modulated signal may not be readily detected.

The impedance measuring apparatus 100 may detect a peak of the amplitude modulated signal at a point A to estimate an amplitude of the baseline signal. The impedance measuring apparatus 100 may detect a phase of the amplitude modulated signal at the point B to estimate a phase of the baseline signal. The impedance measuring apparatus 100 may generate the baseline signal based on information associated with the amplitude and the phase and subtract the baseline signal from the amplitude modulated signal.

After the point B, a subtraction modulated signal obtained by subtracting the baseline signal may appear. The subtraction modulated signal may then include the component of the target signal at a great proportion, and an entire amplitude may be reduced. Thus, additional amplification and higher-resolution impedance measurement may be enabled.

Figure 4:
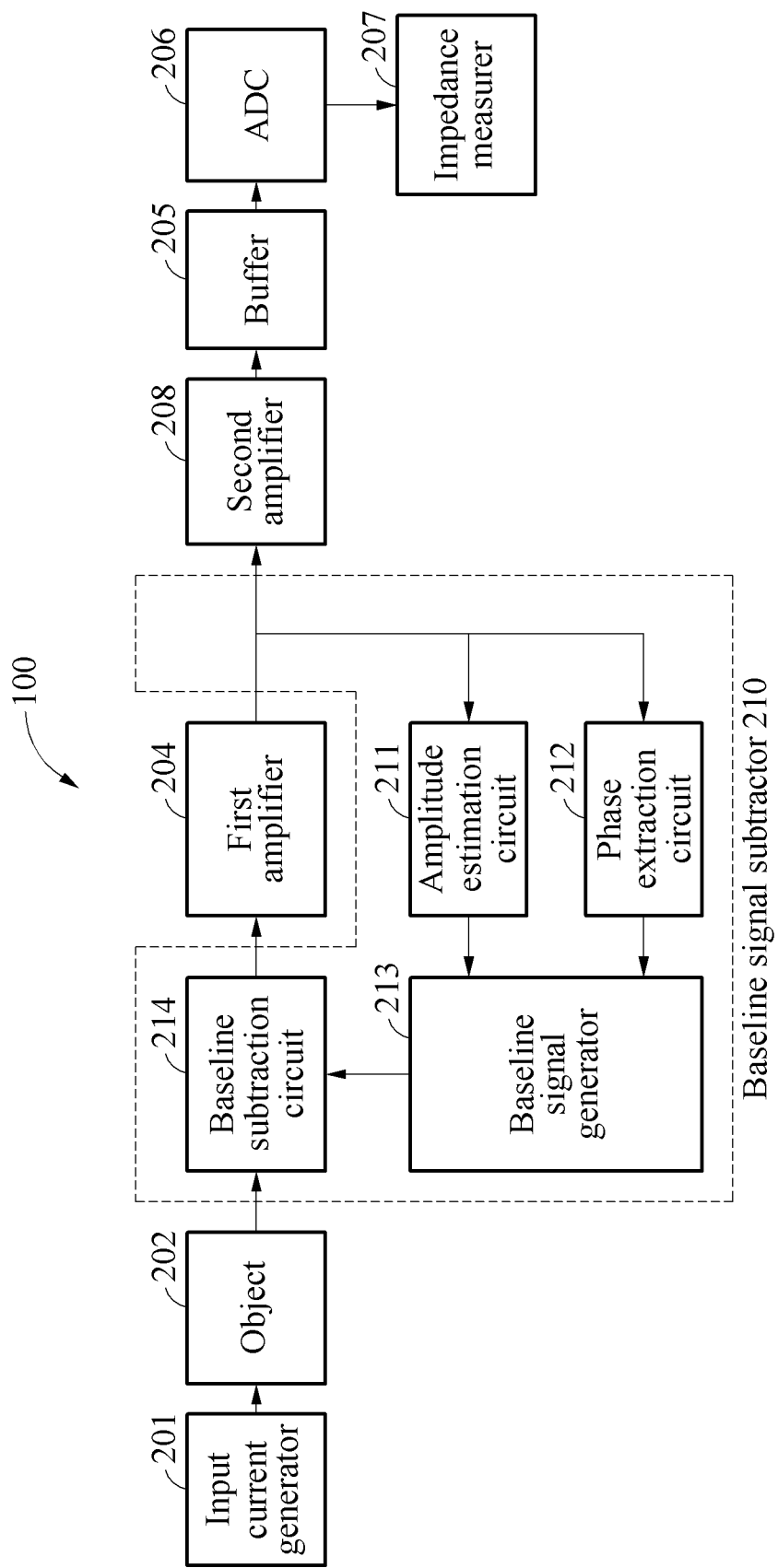
FIG. 4 is a diagram illustrating an example of a configuration of an impedance measuring apparatus including a second amplifier, in accordance with one or more embodiments.

FIG. 4 is a diagram illustrating an example of a configuration of an impedance measuring apparatus including a second amplifier, in accordance with one or more embodiments.

Referring to FIG. 4, the impedance measuring apparatus 100 may include an input current generator 201, a first electrode 226, a second electrode 228, a first amplifier 204, a baseline signal subtractor 210, an ADC 206, and an impedance measurer 207. The impedance measuring apparatus 100 may further include a buffer 205. The baseline signal subtractor 210 includes a baseline signal generator 213 and a baseline subtraction circuit 214. The baseline signal subtractor 210 may further include an amplitude estimation circuit 211, and a phase extraction circuit 212.

In an example, the impedance measuring apparatus 100 may further include a second amplifier 208. The second amplifier 208 may amplify a subtraction modulated signal to output a second amplified signal. A gain of the second amplifier 208 may be adjusted. In such a case, the ADC 206 may convert the second amplified signal to a digital modulated signal.

The second amplifier 208 may include a programmable gain amplifier, for example. When a magnitude of a signal required by an input end of the ADC 206 is not satisfied only by a gain of the first amplifier 204, the second amplifier 208 may further amplify the magnitude of the signal to be greater.

Figure 5:
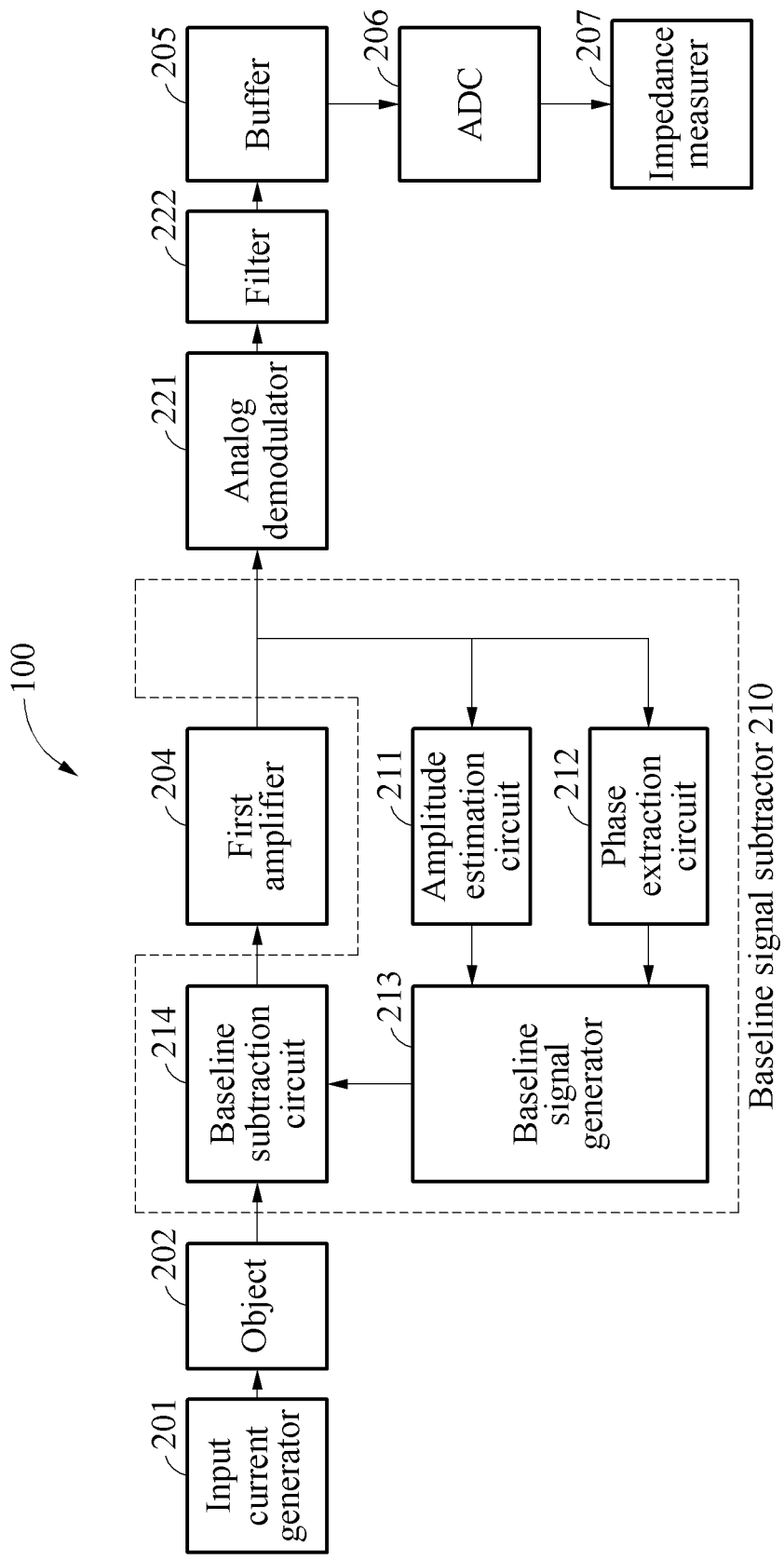
FIG. 5 is a diagram illustrating an example of a configuration of an impedance measuring apparatus including an analog demodulator, in accordance with one or more embodiments.

FIG. 5 is a diagram illustrating an example of a configuration of an impedance measuring apparatus including an analog demodulator, in accordance with one or more embodiments.

Referring to FIG. 5, the impedance measuring apparatus 100 may include an input current generator 201, a first electrode 226, a second electrode 228, a first amplifier 204, a baseline signal subtractor 210, an ADC 206, and an impedance measurer 207. The impedance measuring apparatus 100 may further include a buffer 205. The baseline signal subtractor 210 may include a baseline signal generator 213 and a baseline subtraction circuit 214. The baseline signal subtractor 210 may further include an amplitude estimation circuit 211 and a phase extraction circuit 212.

In an example, the impedance measuring apparatus 100 may further include an analog demodulator 221. The analog demodulator 221 may convert a subtraction modulated signal to a first analog demodulated signal of an impedance frequency by removing a carrier frequency component from the subtraction modulated signal. In such an example, the ADC 206 may convert the first analog demodulated signal to a digital modulated signal.

The impedance measuring apparatus 100 may further include a filter 222. The filter 222 may filter a high-frequency component, excluding an impedance frequency, out of the first analog demodulated signal to output a second analog demodulated signal. In such an example, the ADC 206 may convert the second analog demodulated signal to the digital modulated signal.

Figure 6:
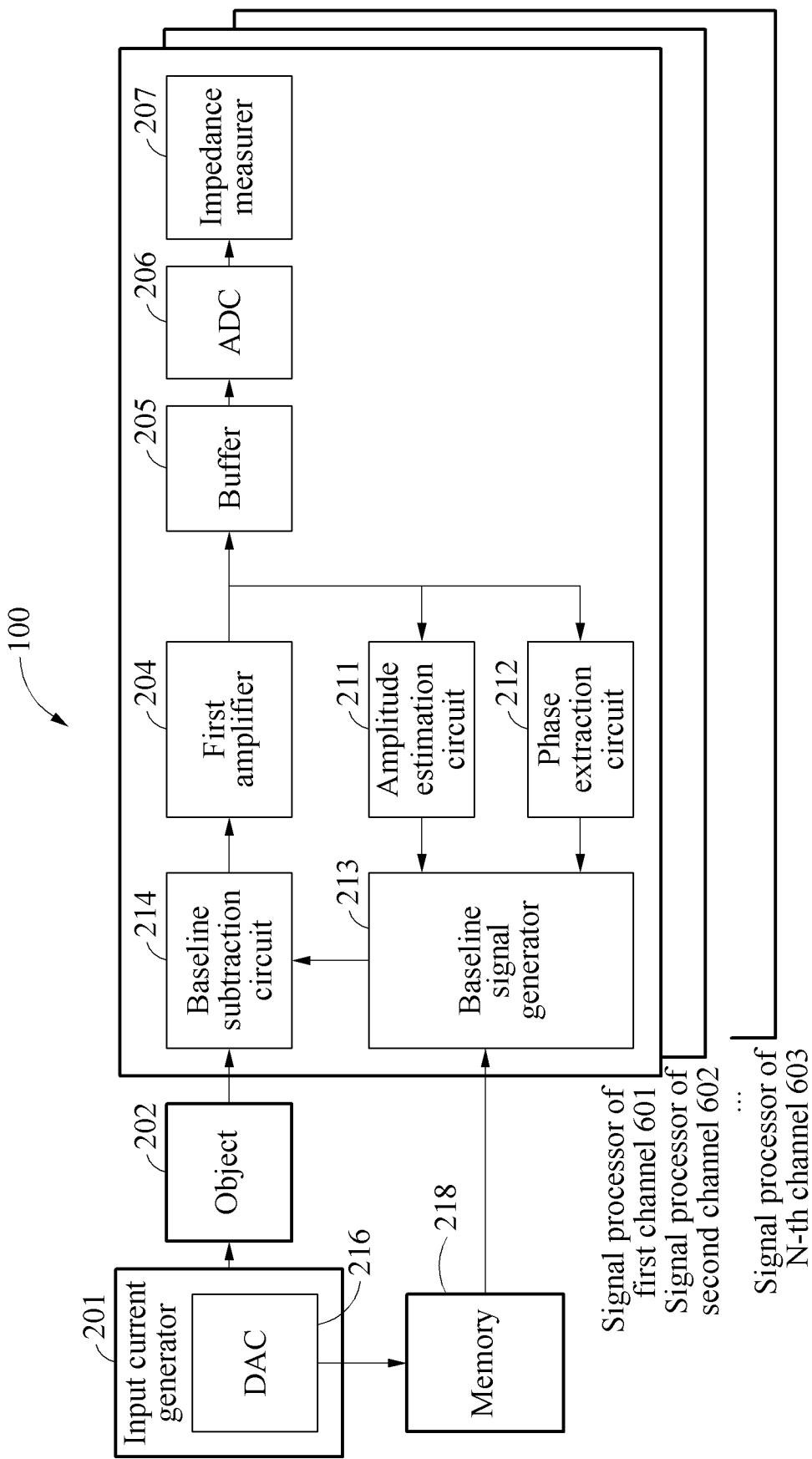
FIG. 6 is a diagram illustrating an example of an impedance measuring apparatus having multiple channels, in accordance with one or more embodiments.

FIG. 6 is a diagram illustrating an example of an impedance measuring apparatus having multiple channels, in accordance with one or more embodiments.

Referring to FIG. 6, the impedance measuring apparatus 100 may include an input current generator 201, a plurality of electrode pairs 226, 228 (FIG. 2), and a plurality of signal processors 601, 602, . . . , and 603 of corresponding channels respectively corresponding to the electrode pairs 226, 228 (FIG. 2). Each of the electrode pairs 226, 228 (FIG. 2) includes a first electrode 226 and a second electrode 228.

Each of the signal processors 601, 602, . . . , and 603 of the corresponding channels may include a first amplifier 204, a baseline signal subtractor (which may include elements 211, 212, 213, and 214), an ADC 206, and an impedance measurer 207. The impedance measuring apparatus 100 may further include a buffer 205. The baseline signal subtractor may include a baseline signal generator 213 and a baseline subtraction circuit 214. The baseline signal subtractor further includes an amplitude estimation circuit 211 and a phase extraction circuit 212.

The input current generator 201 may generate a sinusoidal input signal of a carrier frequency. Each of the electrode pairs 226, 228 (FIG. 2) may apply the sinusoidal input signal to an object 202 having an impedance, and receive an amplitude modulated signal from the object 202.

The input current generator 201 may include a DAC 216 and a memory 218. The DAC 216 may generate the sinusoidal input signal of the carrier frequency. The memory 218 may store an analog level of the sinusoidal input signal. The baseline signal subtractor may generate a baseline signal based on a first amplified signal and the analog level.

The first electrode 226 of each of the electrode pairs 226, 228 may apply the sinusoidal input signal to the object 202 having the impedance. The second electrode 228 of each of the electrode pairs 226, 228 may receive the amplitude modulated signal from the object 202.

The first amplifier 204 of each of the respective signal processors 601, 602, . . . , and 603, may amplify the amplitude modulated signal to output a first amplified signal. The baseline signal subtractor, (which may include elements 211, 212, 213, and 214), may subtract a baseline signal generated based on the first amplified signal from the amplitude modulated signal to output a subtraction modulated signal. The ADC 206 may convert the subtraction modulated signal to a digital modulated signal. The impedance measurer 207 may measure the impedance based on the digital modulated signal.

As described above, the impedance measuring apparatus 100 may store pseudo-sinusoidal analog levels generated in the DAC for generating an input signal, instead of generating a baseline signal by arranging a high-resolution DAC for each channel. Thus, the impedance measuring apparatus 100 may share a single high-resolution signal generator when generating a high-resolution baseline signal in a plurality of channels, and it is thus possible to reduce a size of an area of the impedance measuring apparatus 100 and a cost therefrom.

The input current generator 201, first amplifier 204, ADC 206, impedance measurer 207, buffer 205, amplitude estimation circuit 211, phase extraction circuit 212, baseline signal generator 213, baseline subtraction circuit 214, DAC 216, and memory 218, as well as the remaining apparatuses, units, modules, devices, and other components, described herein may be implemented by hardware components and software components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIM D) multiprocessing, multiple-instruction single-data (MISD) multiprocessing, and multiple-instruction multiple-data (MIMD) multiprocessing.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

Therefore, the scope of the disclosure is defined not by the detailed description, but by the claims and their equivalents, and all variations within the scope of the claims and their equivalents are to be construed as being included in the disclosure.

What is claimed is:

1. An impedance measuring apparatus, comprising:
   an input current generator, configured to generate a sinusoidal input signal of a carrier frequency;
   a first electrode, configured to apply the sinusoidal input signal to an object which has an impedance;
   a second electrode, configured to receive an amplitude modulated signal from the object;
   a first amplifier, configured to amplify the received amplitude modulated signal and output a first amplified signal;
   a baseline signal subtractor, configured to subtract a baseline signal generated based on the first amplified signal from the amplitude modulated signal, and output a subtraction modulated signal;
   an analog-to-digital converter (ADC), configured to convert the subtraction modulated signal to a digital modulated signal; and
   an impedance measurer, configured to measure the impedance based on the digital modulated signal.

2. The apparatus of claim 1, wherein the baseline signal subtractor comprises:
   a baseline signal generator, configured to generate the baseline signal based on the first amplified signal; and
   a baseline subtraction circuit, configured to subtract the baseline signal from the amplitude modulated signal.

3. The apparatus of claim 2, wherein the baseline signal generator comprises:
   an amplitude estimation circuit, configured to estimate an amplitude of the baseline signal from the first amplified signal; and
   a phase extraction circuit, configured to extract a phase of the baseline signal from the first amplified signal.

4. The apparatus of claim 1, further comprising:
   a digital demodulator configured to convert the digital modulated signal to a digital demodulated signal of an impedance frequency by removing a component of the carrier frequency from the digital modulated signal,
     wherein the impedance measurer is configured to measure the impedance based on the digital demodulated signal.

5. The apparatus of claim 1, further comprising:
a buffer, configured to receive the subtraction modulated signal, and output the received subtraction modulated signal.

6. The apparatus of claim 1, further comprising:
a second amplifier, configured to amplify the subtraction modulated signal, and output a second amplified signal,
wherein the ADC is configured to convert the second amplified signal to the digital modulated signal, and
wherein a gain of the second amplifier is adjustable.

7. The apparatus of claim 1, further comprising:
an analog demodulator, configured to convert the subtraction modulated signal to a first analog demodulated signal of an impedance frequency by removing a component of the carrier frequency from the subtraction modulated signal,
wherein the ADC is configured to convert the first analog demodulated signal to the digital modulated signal.

8. The apparatus of claim 7, further comprising:
a filter, configured to filter a high-frequency component that excludes the impedance frequency out of the first analog demodulated signal, and output a second analog demodulated signal,
wherein the ADC is configured to convert the second analog demodulated signal to the digital modulated signal.

9. An impedance measuring apparatus, comprising:
an input current generator, configured to generate a sinusoidal input signal of a carrier frequency;
a plurality of electrode pairs configured to apply the sinusoidal input signal to an object which has an impedance, and receive an amplitude modulated signal from the object; and
one or more signal processors corresponding to a channel corresponding to each of the electrode pairs,
wherein each of the electrode pairs comprises:
a first electrode, configured to apply the sinusoidal input signal to the object which has the impedance; and
a second electrode, configured to receive the amplitude modulated signal from the object, and
the signal processor comprises:
a first amplifier, configured to amplify the amplitude modulated signal and output a first amplified signal;
a baseline signal subtractor, configured to subtract a baseline signal generated based on the first amplified signal from the amplitude modulated signal, and output a subtraction modulated signal;
an analog-to-digital converter (ADC), configured to convert the subtraction modulated signal to a digital modulated signal; and
an impedance measurer, configured to measure the impedance based on the digital modulated signal.

10. The apparatus of claim 9, wherein the input current generator comprises:
a digital-to-analog converter (DAC) configured to generate the sinusoidal input signal of the carrier frequency; and
a memory configured to store an analog level of the sinusoidal input signal,
wherein the baseline signal subtractor is configured to generate the baseline signal based on the first amplified signal and the analog level.

11. An impedance measuring method of an impedance measuring apparatus, the method comprising:
generating, by an input current generator, a sinusoidal input signal of a carrier frequency;
applying, by a first electrode, the sinusoidal input signal to an object;
receiving, by a second electrode, an amplitude modulated signal from the object;
amplifying, by an amplifier the received amplitude modulated signal to output a first amplified signal;
subtracting, by a baseline signal subtractor, a baseline signal generated based on the first amplified signal from the amplitude modulated signal, and output a subtraction modulated signal;
converting, by an analog-to-digital (ADC), the subtraction modulated signal to a digital modulated signal; and
measuring, by an impedance measurer, the impedance based on the digital modulated signal.

12. The method of claim 11, wherein the baseline signal is generated based on the amplitude modulated signal from the object, and
wherein the baseline signal is subtracted from the amplitude modulated signal to measure the impedance of the object.

13. The method of claim 12, wherein the impedance of the object is measured through a plurality of channels corresponding to a plurality of electrode pairs.

* * * * *